United States Patent
Seto et al.

(10) Patent No.: US 6,171,829 B1
(45) Date of Patent: Jan. 9, 2001

(54) PHYSIOLOGICALLY ACTIVE SUBSTANCE PF1191 AND PROCESS FOR PRODUCING THE SAME

(75) Inventors: Haruo Seto; Kazuo Shin-Ya, both of Tokyo; Takashi Yaguchi; Toru Sasaki, both of Kanagawa, all of (JP)

(73) Assignee: Meiji Seika Kaisha, Ltd., Tokyo (JP)

( * ) Notice: Under 35 U.S.C. 154(b), the term of this patent shall be extended for 0 days.

(21) Appl. No.: 09/380,823

(22) PCT Filed: Mar. 12, 1998

(86) PCT No.: PCT/JP98/01046

§ 371 Date: Sep. 10, 1998

§ 102(e) Date: Sep. 10, 1999

(87) PCT Pub. No.: WO98/41503

PCT Pub. Date: Sep. 24, 1998

(30) Foreign Application Priority Data

Mar. 14, 1997 (JP) .................................................. 9-060311

(51) Int. Cl.⁷ .......................... C07D 207/12; C12P 21/04
(52) U.S. Cl. ........................ 435/71.2; 435/107; 562/443; 548/532
(58) Field of Search ........................... 548/532; 562/443; 435/71.2, 107

(56) References Cited

U.S. PATENT DOCUMENTS 5,342,946   8/1994   Hamilton ................................. 546/23

FOREIGN PATENT DOCUMENTS

WO 96/10023   4/1996   (EP) .

OTHER PUBLICATIONS

International Search Report (May 24, 1999).
Tetrahedron Letters, vol. 38, No. 40, Oct. 1997, pp. 7079–7082, "Structure of Kaitocephalin, A Novel Glutamate Receptor Antagonist Produced by *Eupenicillium Shearii*", Shin–Ya, K. et al.
European Search Report (Apr. 13, 2000).

*Primary Examiner*—Joseph K. McKane
*Assistant Examiner*—Jane C. Oswecki
(74) *Attorney, Agent, or Firm*—Sughrue, Mion, Zinn, Macpeak & Seas, PLLC

(57) ABSTRACT

A substance PF1191 having an inhibitory activity to kainic acid toxicity represented by the following formula (I) which is obtained by incubating a fungus belonging to the genus Eupenicillium and isolating the product thus produced from the culture by solvent extraction, adsorption column chromatography, gel filtration, etc.

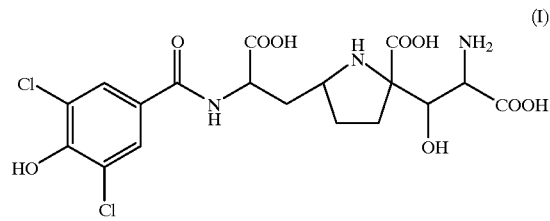

2 Claims, No Drawings

PHYSIOLOGICALLY ACTIVE SUBSTANCE PF1191 AND PROCESS FOR PRODUCING THE SAME

This application is a 371 of PCT/JP98/01046 filed Mar. 12, 1998.

TECHNICAL FIELD

This invention relates to a novel physiologically active substance PF1191 showing an inhibitory activity to kainic acid toxicity and thus being useful as a remedy and a preventive for diseases caused by nervous disturbances or its salt, and a process for producing the same.

BACKGROUND ART

Excitatory amino acids (glutamic acid, aspartic acid, etc.) play important roles as neurotransmitters in mammals. On the other hand, there have been reported findings one after another that abnormal excitation of excitatory amino acid receptors is one of the causative factors of nerve cell death occurring in brain ischemia, head injury, Alzheimer's disease, Parkinson's disease, Huntington's chorea, etc. It is also suggested that abnormalities in these excitatory amino acid receptors participate in the onset of schizophrenia. Under these circumstances, studies have been vigorously made on excitatory amino acid receptor antagonists and agonists.

Regarding substances with antagonism to excitatory amino acid receptors with microbial origin, it is reported that a substance ES-242 is produced by Verticillium sp. ES-242 (J. Antibiotics, vol. 45, 88–93 (1992)).

To develop an antagonist to excitatory amino acid receptors, the present inventors have studied and searched to find a substance originating in a microbial product which is capable of inhibiting the toxicity of kainic acid on brain nerve cells.

It is also reported that kainic acid is toxic to primarily cultured chick telencephalon nerve cells and this toxicity by the excitatory amino acid is expressed via the cystine transporter system and non-N-methyl-D-aspartic acid (NMDA) receptor (Neuroscience Letters, vol. 139, 205–208 (1992)). This toxicity is inhibited by non-NMDA receptor antagonists including 6-cyano-7-nitroquinoxaline-2,3-dione (CNQX), 6,7-dinitroquinoxaline-2,3-dione (DNQX) and 6-nitro-7-sulfamoylbenzo[f]quinoxaline-2,3-dione (NBQX).

Accordingly, the present invention aims at providing a substance which is capable of inhibiting the toxicity of kainic acid on brain nerve cells and therefore useful as a remedy and a preventive for diseases caused by nervous disturbances.

DISCLOSURE OF THE INVENTION

By using primarily cultured chick telencephalon nerve cells, the present inventors searched microbial products to find out a substance capable of inhibiting the toxicity of kainic acid on brain nerve cells. As a result, they found that a strain belonging to the genus Eupenicillium accumulated a product having an inhibitory activity to kainic acid toxicity in its culture medium. Next, the above product (i.e., the substance PF1191) was isolated and purified from the culture and identified as a novel substance based on its physicochemical properties. As the results of the subsequent studies, it was confirmed that this substance PF1191 has a stronger inhibitory activity to kainic acid toxicity than that of DNQX. The present invention has been completed based on these findings.

Accordingly, the first gist of the present invention resides in the provision of a novel substance PF1191, which is represented by the following formula (I) and involves all stereoisomers thereof, or its salt:

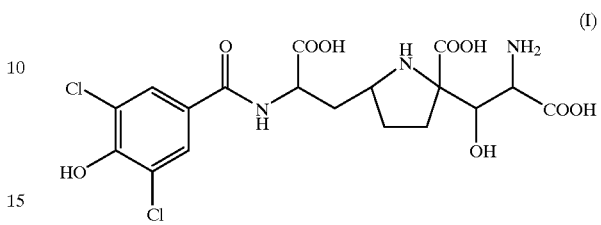

The second gist of the present invention resides in the provision of a process for producing the physiologically active substance PF1191 or its salt which comprises incubating a fungus belonging to the genus Eupenicillium and being capable of producing the substance PF1191, and collecting the thus produced substance PF1191 from the culture.

MODE FOR CARRYING OUT THE INVENTION

The microorganism to be used in the production of the substance PF1191 in the present invention may be an arbitrary one so long as it belongs to the genus Eupenicillium and is capable of producing the substance PF1191. As an example of the microorganism usable in the present invention, a strain *Eupenicillium shearii* PF1191 (hereinafter referred to as the "PF1191 strain") having been newly isolated from the soil may be cited.

1. Mycological Properties of PF1191 Strain (1) Characteristics in Incubation

Colonies grow well on Czapek-yeast extract agar and attain 35 to 40 mm in diameter after incubating at 25° C. for 7 days. They are a white to grayish brown, velvety, radial wrinkled and consisting of a thick mycelial layer. A number of ascomata are formed in submerged hyphae. It has a back face in a pale olive color.

Colonies grow well on malt extract agar and attain 18 to 20 mm in diameter after incubating at 25° C. for 7 days. They are pale brown, velvety, flat and consisting of thin mycelial layer. A number of ascomata are formed in submerged hyphae. It has a back face in a pale orange color.

Colonies grow well on oatmeal agar and attains 18 to 20 mm in diameter after incubating at 25° C. for 7 days. They are grayish brown, velvety, flat and consisting of thin mycelial layer. A number of ascomata are formed on the colony surface to give a granular appearance. It has a back face in a pale yellowish brown color.

At an incubation temperature of 37° C., the growth of the strain is inferior in each of the above-described media to the growth at 25° C.

(2) Morphological Characteristics

Cleistochecia are globose to ellipsoidal, yellowish brown and 150 to 350 µm in diameter. Each peridium is composed of sclerenchyma cells and turns from pseudoparenchyma into sclerotium. They take 3 to 4 weeks for maturation. Asci are globose to ellipsoidal in shape, 6 to 8×5 to 6.5 µm in size, 8-spored and evanescent at maturity. Ascospores are lens-shaped and 3.0 to 3.5×2.0 to 3.0 µm in size, each having two equatorial crests and fine projections on the convex surface. Conidiophores are 200 to 600×2 to 2.5 µm in size and smooth-walled. Penicilli are biverticillate, metulae are 12 to 20×2.5 to 3 μm in size and 2 to 4 per stipe, and phialides are ampulliform, 7 to 12×2.5 to 3 μm in size and 5 to 7 per metula. Conidia are ellipsoidal in shape and 2.5 to 3×2 to 2.5 μm in size and smooth-walled.

Based on these mycological characteristics, this strain has been identified as *Eupenicillium shearii* belonging to Plectomycetes and named *Eupenicillium shearii* PF1191 strain. In the identification, use was made of "The ascomycete genus Eupenicillium and related Penicillium anamorphs (Studies in Mycology, No. 23)", Amelia C. Stolk and Robert A. Samson, Centraal-bureau voor Schimmelcultures, 1983.

This PF1191 strain has been deposited as follows.
① Depository name: International Depository, National Institute of Bioscience and Human-Technology, Agency of Industrial Science and Technology
Address: 1–3, Higashi 1-chome, Tsukuba-shi, Ibaragi, 305-8566 JAPAN
② Deposition Date: Original deposition date: Dec. 2, 1996
Request for transfer: Feb. 20, 1998 (transferred from FERM P-15973 deposited on Dec. 2, 1996)
③ Deposition No. FERM BP-6263.

Similar to other funguses, the PF1191 strain is liable to undergo changes in its properties. Therefore, use can be made in the present invention of, for example, mutants (either spontaneous ones or mutagenized ones) originating in the PF1191 strain, conjugants or gene recombinants, so long as they are capable of producing the substance PF1191.

2. Method for Incubating Substance PF1191-producing Strain

The microorganism capable of producing the substance PF1191 may be incubated in a medium containing nutrients commonly usable by microorganisms. As the nutrients, use can be made of those conventionally employed in the incubation of funguses. Examples of carbon sources usable herein include glucose, sucrose, starch syrup, dextrin, starch, glycerol, molasses, animal oils and vegetable oils. Examples of the nitrogen sources include organic matters such as soybean meal, wheat germ, corn steep liquor, cotton seed meal, meat extract, peptone, yeast extract, ammonium sulfate, sodium nitrate and urea. Furthermore, it is possible to add to the medium inorganic salts capable of providing ions of sodium, potassium, calcium, magnesium, cobalt, chlorine, phosphate, sulfate, etc. The medium may furthermore contain appropriate organic and inorganic matters promoting the growth of the strain and accelerating the production of the substance PF1191.

Regarding the incubation method, it is most desirable to employ aerobic culture, in particular, stand culture. Although the incubation may be appropriately performed at 25 to 30° C., it is carried out at around 26° C. in most cases. The productivity of the substance PF1191 varies depending on the medium and incubation conditions. The accumulation of the substance PF1191 attains the maximum level usually after incubating for 2 to 14 days either in stand culture, shaking culture or tank culture. When the accumulation of the substance PF1191 in the liquid culture medium attains the maximum level, the incubation is ceased and the target product is isolated and purified from the medium.

The substance PF1191 according to the present invention produced by the above-described process is purified in the following manner.

By taking advantage of the properties, the substance PF1191 can be extracted and purified by using separating operations commonly employed in the art, for example, solvent extraction, ion exchange resin method, adsorption or partition column chromatography, gel filtration, dialysis and precipitation, either alone or appropriately combinedly. More particularly speaking, a water-miscible solvent (methanol, ethanol, acetone, etc.) is added to the culture followed by stirring to give an extract of the substance PF1191. After evaporating off the organic solvent from the extract, the target substance PF1191 with a high purity can be purified from the residual aqueous solution by appropriately combining, for example, adsorption/desorption with the use of an adsorbent, molecular partition with the use of a gel filtration agent, recrystallization from an appropriate solvent, high-performance liquid chromatography, etc. For example, the substance PF1191 can be purified by subjecting the above-described aqueous solution successively to activated charcoal column chromatography, gel filtration chromatography, and liquid chromatography with the use of an ODS column.

Salts of the substance PF1191 include metal salts (for example, alkali metal salts such as sodium salt, alkaline metal salts such as calcium salt, etc.) and base addition salts formed together with pharmaceutically acceptable inorganic or organic bases.

BEST MODE FOR CARRYING OUT THE INVENTION

Now, examples of the embodiment of the present invention will be described. Since the present invention has clarified the properties of the substance PF1191, various processes for producing the substance PF1191 can be devised on the basis of its properties. Accordingly, it should be understood that the present invention is not construed as being limited to these examples but involves not only modifications of the processes disclosed in the examples but also any methods for producing, extracting and purifying the substance PF1191 with the use of publicly known operations based on the properties of the substance PF1191 having been disclosed by the present invention.

EXAMPLE 1

A medium (pH 7.0 before sterilization) consisting of 2.0% of starch, 1.0% of glucose, 0.5% of peptone, 0.6% of wheat germ, 0.3% of yeast extract, 0.2% of soybean meal and 0.2% of calcium carbonate was used as a seed medium. A solid medium prepared by adding 2.5% of soybean meal to sufficiently water-soaked rice was used as a production medium.

20 ml of the above-described seed medium was put into a 100 ml Erlenmeyer flask followed by sterilization at 120° C. for 15 minutes. Next, one platinum loopful of the strain PF1191 grown on a slant agar medium was inoculated thereinto and incubated under shaking at 25° C. for 4 days. Then 30 g of the above-described production medium was put into another 100 ml Erlenmeyer flask followed by sterilization at 120° C. for 15 minutes. After inoculating with 1 ml of the seed culture described above, the flask was well stirred and incubated as stationary culture at 28° C. for 14 days. 3 kg of the thus obtained culture was extracted with a 67% aqueous solution of acetone for 1 hour to give 10 L of a cell extract.

EXAMPLE 2

After evaporating off acetone from the cell extract obtained as in Example 1, the active component contained in the residual aqueous solution was adsorbed on an activated charcoal column (50 mm in radius×400 mm in height). After washing the activated charcoal column with water, the active component was eluted with a 50% aqueous solution of acetone. The eluate thus obtained was concentrated and then adsorbed on a column (50 mm in radius×450 mm in height)

packed with TOYOPEARL HW-40F (manufactured by Tosoh Corporation) and gel filtration chromatography was performed by using a 60% aqueous solution of methanol as a developing solvent. After concentrating the active fractions, the active component was adsorbed on a column (35 mm in radius×600 mm in height) packed with PEGASIL ODS (manufactured by Senshu Science) and column chromatography was performed with the use of a 20% aqueous solution of methanol as a developing solvent. The active fractions thus obtained were combined and concentrated to give a crude powder containing the active component. This crude powder was further purified by high performance liquid chromatography (column: PEGASIL ODS, 20 mm in radius×250 mm in height) by using a 20 mM diethylamine carbonate buffer solution containing 5% of methanol as a developing solution. Thus, 9.2 mg of the pure substance PF1191 was obtained.

The thus obtained substance PF1191 according to the present invention have the following properties.
(1) Color and form: Colorless powder.
(2) Molecular formula: $C_{18}H_{21}N_3O_9Cl_2$.
(3) Mass spectrum (HRFAB-MS): found 494.0757[M+H]$^+$ calcd. 494.0733.
(4) Melting point: 235–238° C. (decomp.).
(5) Specific rotation: $[\alpha]_D^{21}$=−30.9° (c 0.7, H$_2$O).
(6) UV absorption spectrum:
In aq. solution $\lambda_{max}(\epsilon)$ 217(18,200), 297(8,200) nm.
In 0.01N HCl $\lambda_{max}(\epsilon)$ 214(23,200), 255(6,700) nm.
(7) Infrared absorption spectrum:
ν(KBr cm$^{-1}$): 3410, 1640, 1560, 1485, 1385.
(8) Nuclear magnetic resonance spectra: $^1$H and $^{13}$C NMR spectra in D$_2$O are as follows.
(a) $^1$H NMR spectrum $\delta_H$(ppm) 7.62(2H), 4.41(1H), 4.35(1H), 4.16(1H), 3.70(1H), 2.41(1H), 2.28(1H), 2.12(1H), 2.06(1H), 2.01(1H), 1.61(1H).
(b) $^{13}$C NMR spectrum $\delta_C$(ppm) 177.8 m 175.0, 171.3, 168.2, 153.8, 128.6, 125.5, 123.0, 77.1, 71.4, 59.7, 56.2, 54.2, 35.6, 32.7, 30.4.
(9) High performance liquid chromatography:
Column: PEGASIL ODS (manufactured by Senshu Science, 4.6 mm in diameter×250 mm in height).
Mobile phase: 20 mM diethylamine carbonate buffer containing 5% of methanol.
Flow rate: 1 ml/min.
Detector: UV 300 nm.
Retention time: 6.1 min.
Based on these data, it is considered that the substance PF1191 has the following structure.

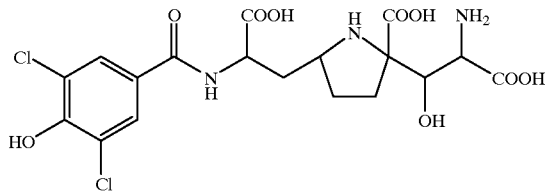

TEST EXAMPLE

The inhibitory activities to kainic acid toxicity of the substance PF1191 on primarily cultured nerve cells of chick telencephalon and rat hippocampus were examined. The results were as follows. The test with the use of the primarily cultured nerve cells of chick telencephalon was carried out in accordance with the method reported in Neuroscience Letters, vol. 139, 205–208 (1982), while the test with the use of the primarily cultured nerve cells of rat hippocampus was carried out in accordance with the method reported in Brain Research, 126(1977) 397–425.

The molar concentration at which the cytotoxicity caused by the addition of 500 μM of kainic acid to the cultured cells was inhibited at a ratio of 50% was expressed in EC$_{50}$ (effective concentration-fifty) in Table 1 below.

TABLE 1

Inhibitory activity to kainic acid toxicity of the substance PF1191

| | 50% Effective conc. (EC$_{50}$: μM) | |
|---|---|---|
| Cell and Agonist | Substance PF1191 | DNQX |
| primarily cultured nerve cells of chick telencephalon + kainic acid (500 μM) | 1.5 | 7.5 |
| primarily cultured nerve cells of rat hippocampus + kainic acid (500 μM) | 0.45 | 1.8 |

DNQX: 6,7-dinitroquinoxaline-2,3-dione.

It was thus confirmed that the substance PF1191 showed stronger inhibitory activity to kainic acid toxicity in comparison with the known substance DNQX in each test.

The novel substance PF1191 provided by the present invention has an activity of inhibiting the toxicity of kainic acid on nerve cells and, therefore, is useful as a remedy and a preventive for diseases caused by nervous disturbances such as brain ischemia.

Industrial Applicability

The present invention provides a novel substance PF1191 having an activity of inhibiting the toxicity of kainic acid on nerve cells. This substance PF1191 is useful as a nerve cell protective agent against nerve cytotoxicity of excitatory amino acids formed in, for example, brain ischemia.

What is claimed is:
1. A substance PF1191 represented by the following formula (I) or its salt:

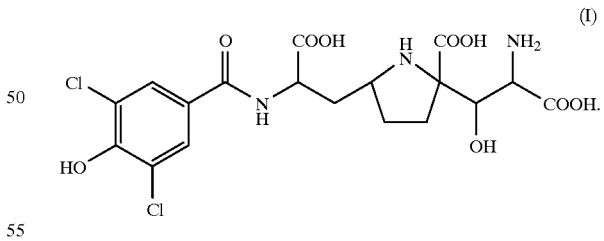

2. A process for producing the substance PF1191 or its salt which comprises incubating a microorganism belonging to the genus Eupenicillium and being capable of producing the physiologically active substance PF1191, and collecting the substance PF1191 as claimed in claim 1 from the culture.

* * * * *